United States Patent [19]

Audia et al.

[11] Patent Number: 5,698,571
[45] Date of Patent: Dec. 16, 1997

[54] 5-HT$_{1F}$ MEDIATED INHIBITION OF NEUROGENIC MENINGEAL EXTRAVASATION: A METHOD FOR THE TREATMENT OF MIGRAINE

[75] Inventors: James E. Audia, Indianapolis; Marlene L. Cohen, Carmel; Kirk W. Johnson, Indianapolis; Lee A. Phebus, Fountaintown, all of Ind.; Theresa Branchek, Teaneck, N.J.

[73] Assignee: Eli Lilly and Company, Indianapolis, Ind.

[21] Appl. No.: 318,330

[22] Filed: Oct. 5, 1994

[51] Int. Cl.$^6$ .............. A61K 31/445; A61K 31/405; A61K 31/40; A61K 31/13

[52] U.S. Cl. .............. 514/323; 514/250; 514/411; 514/415; 514/657

[58] Field of Search .............. 514/323, 415, 514/657, 411, 250

[56] References Cited

FOREIGN PATENT DOCUMENTS

WO 93/14201 7/1993 WIPO.

OTHER PUBLICATIONS

Lee et al., American Journal of Physiology, 266 (3 Pt. 2) H1000–6, 1994.

Moskowitz, M.A., *TiPS*, 13 (8), 307–311 (1972).

Moskowitz, M.A., and Macfarlane, Robert, *Cerebrovascular and Brain Metabolism Reciews*, 5, 159–177 (1993).

Fozard, J.R., "Migraine: A Spectrum of Ideas", Sandler, M., and Collins, G.M. (eds.), Oxford University Press: New York (1990).

Moskowitz, M.A., *Neurology*, 43 (Suppl 3), 16–20 (1993).

Silberstein, S.D., *Headache*, 34, 408–417 (1994).

Adham, et al., *Prac. Natl. Acad. Sci.*, 90, 408–412 (1993).

*Primary Examiner*—Phyllis G. Spivack
*Attorney, Agent, or Firm*—Robert D. Titus; David E. Boone

[57] ABSTRACT

The present invention provides a method for the treatment of migraine with compounds or compositions that are selective agonists of 5-HT$_{1F}$ receptors relative to other serotonin receptors that produce unwanted effects like vasoconstriction. The neurogenic meningeal extravasation that leads to the pain of migraine is inhibited.

20 Claims, No Drawings

5-HT$_{1F}$ MEDIATED INHIBITION OF NEUROGENIC MENINGEAL EXTRAVASATION: A METHOD FOR THE TREATMENT OF MIGRAINE

BACKGROUND OF THE INVENTION

The diverse physiological activity exhibited by the neurotransmitter serotonin (5-HT) is mediated by at least seven receptor classes: 5-HT$_1$, 5-HT$_2$, 5-HT$_3$, 5-HT$_4$, 5-HT$_5$, 5-HT$_6$ and 5-HT$_7$. The most heterogeneous of these classes appears to be 5-HT$_1$, subclassified as: 5-HT$_{1A}$, 5-HT$_{1B}$, 5-HT$_{1C}$, 5-HT$_{1D}$ (Hamon et al., *Neuropsychopharmacol.*, 3(5/6), 349–360 (1990)) and 5-HT$_{1E}$ (Leonhardt et al., *J. Neurochem.*, 53(2), 465–471 (1989)). A human gene which expresses an additional 5-HT$_1$ subclass, 5-HT$_{1F}$, was isolated by Kao and coworkers (*Proc. Natl. Acad. Sci. USA*, 90, 408–412 (1993)). This 5-HT$_{1F}$ receptor has been shown to exhibit a pharmacological profile distinct from any serotonergic receptor yet described.

Theories regarding the pathophysiology of migraine have been dominated since 1938 by the work of Graham and Wolff (*Arch. Neurol. Psychiatry*, 39, 737–63 (1938)). They proposed that the cause of migraine headache is vasodilatation of extracranial vessels. This view is supported by knowledge that ergot alkaloids and sumatriptan contract cephalic vascular smooth muscle and are effective in the treatment of migraine. Sumatriptan is a hydrophilic agonist at 5-HT-1-like receptors and does not cross the blood-brain barrier (Humphrey, et al., *Ann. NY Acad. Sci.*, 600, 587–600 (1990)). Recently several new series of compounds said to be useful for the treatment of migraine have been described in WO94/03446, WO93/11106, WO92/13856, EP0438230 and WO91/18897. Each of these series of compounds has been developed to optimize the 5-HT$_1$-like mediated vasoconstrictive activity of sumatriptan. Sumatriptan's contraindications, coronary vasospasm, hypertension and angina, however, are also products of its vasoconstrictive activity (MacIntyre, P. D., et al., *British Journal of Clinical Pharmacology*, 34, 541–546 (1992); Chester, A. H., et al., *Cardiovascular Research*, 24, 932–937 (1990); Conner, J. E., et al., *European Journal of Pharmacology*, 161, 91–94 (1990)).

While this vascular mechanism for migraine has gained wide acceptance, there is not total agreement as to its validity. Moskowitz has shown, for example, that the occurrence of migraine headaches is independent of changes in vessel diameter (*Cephalalgia*, 12, 5–7, (1992)). Furthermore, Moskowitz has proposed that currently unknown triggers stimulate trigeminal ganglia which innervate vasculature within cephalic tissue, giving rise to release of vasoactive neuropeptides from axons on the vasculature. These released neuropeptides then initiate a series of events leading to neurogenic inflammation, a consequence of which is pain. This neurogenic inflammation is blocked by sumatriptan and ergot alkaloids at a dose similar to that required to treat acute migraine in humans. While this blockade of neurogenic protein extravasation is believed to be mediated by 5-HT$_{1D}$ receptors, the effective dosages of 5-HT$_{1D}$ selective compounds do not correlate with in vitro binding at the 5-HT$_{1D}$ binding site. The lack of correlation suggests that a receptor subtype other than 5-HT$_{1D}$ may mediate the effects of sumatriptan (*Neurology*, 43(suppl. 3), S16-S20 (1993)). In addition, it has been reported that α, H$_3$, µ-opioid and somatostatin receptors may also be located on trigeminovascular fibers and may block neurogenic plasma extravasation (Matsubara et al., *Eur. J. Pharmacol.*, 224, 145–150 (1992)). Weinshank et al. have reported that sumatriptan and several ergot alkaloids have a high affinity for the 5-HT$_{1F}$ receptor, suggesting a role for the 5-HT$_{1F}$ receptor in migraine (WO93/14201).

SUMMARY OF THE INVENTION

The present invention provides a method for treatment of migraine and related disorders in mammals, comprising administering an effective amount of a 5-HT$_{1F}$ agonist or a composition exhibiting 5-HT$_{1F}$ agonist activity, which also exhibits minimal vasoconstrictive effects.

DETAILED DESCRIPTION OF THE INVENTION

The present invention provides a method for the treatment of migraine and associated disorders which relies on a novel mechanism of action. By treating a migraineur with a compound or composition which is a selective agonist at the 5-HT$_{1F}$ receptor relative to other serotonin receptors which produce unwanted effects like vasoconstriction, the neurogenic meningeal extravasation which leads to the pain of migraine is inhibited and the physiological liabilities of compounds exhibiting vasoconstriction or other side effects are avoided. This mechanism is operative in mammals and the preferred mammal is a human.

A further embodiment of this invention comprises the administration of a composition which exhibits selective 5-HT$_{1F}$ agonist activity. The composition may be composed of one or more agents which, individually or together, are selective agonists of 5-HT$_{1F}$ receptors relative to other serotonin receptors which produce unwanted effects like vasoconstriction.

The term "5-HT$_{1F}$ agonist", as it is used in the description of this invention, is taken to mean a full or partial agonist. A compound which is a partial agonist at the 5-HT$_{1F}$ receptor must exhibit sufficient agonist activity to inhibit neurogenic meningeal extravasation at an acceptable dose. While a partial agonist of any intrinsic activity may be useful for the method of this invention, partial agonists of at least about 50% agonist effect (E$_{max}$) are preferred and partial agonists of at least about 80% agonist effect (E$_{max}$) are more preferred. Full agonists at the 5-HT$_{1F}$ receptor are most preferred.

Inhibition of neuronal protein extravasation alone is a necessary but not sufficient condition for the method of this invention. The method of this invention further requires that only minimal vasoconstriction occurs at a dose effective for inhibition of neuronal protein extravasation. The ratio of vasoconstriction EC$_{50}$ in the rabbit saphenous vein to inhibition of neuronal protein extravasation ID$_{50}$ in the guinea pig is defined as the Specificity Index. The Specificity Index calculated from these assays identifies compounds or compositions which are able to distinguish between these physiological events. The panel of compounds used to prove the principle of the invention and the pharmacological assays required to determine the Specificity Index are described below.

3-[2-(dimethylamino)ethyl]-N-methyl-1H-indole-5

Compound I -methanesulfonamide butane-1,4-dioate (1:1)

(Sumatriptan succinate)

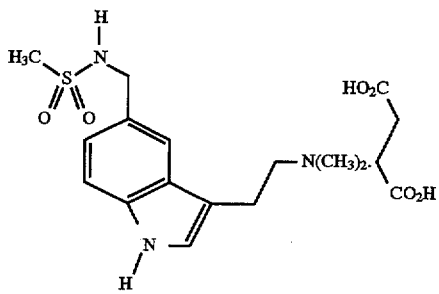

Sumatriptan succinate is commercially available as Imitrex® or may be prepared as described in U.S. Pat. No. 5,037,845, issued Aug. 6, 1991, which is herein incorporated by reference.

Compound II 5-fluoro-3-<1-<2-<1-methyl-1H-pyrazol-4-yl>ethyl>-4-piperidinyl>-1H-indole hydrochloride

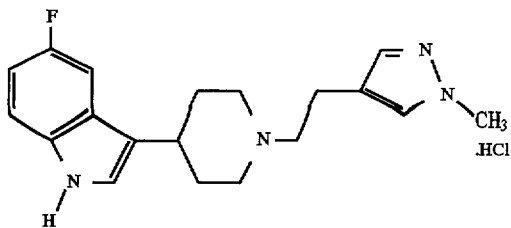

Compound II is available by the following procedure.

2-(1-methyl-3-pyrazolo)-1-ethanol

To a mixture of 200 gm (2.85 mole) 2,3-dihydrofuran and 800 mL (4.81 mole) triethylorthoformate were added 0.8 mL (6.5 mMol) boron trifluoride diethyl etherate dropwise. After an initial exotherm the reaction mixture was allowed to stir at ambient temperature for four days. To the reaction mixture was then added 4.0 gm potassium carbonate and the reaction mixture was distilled under 6.0 mm Hg. Fractions distilling between 60° C. and 130° C. were collected to give 261.64 gm (42.1%) of a light yellow oil.

MS (m/e): 219(M+)

To a solution of 87.2 gm (0.40 mole) of the previously prepared yellow oil in 787 mL 1N HCl were added 21.3 mL (0.40 mole) methyl hydrazine and the reaction mixture was stirred at reflux for four hours. The reaction mixture was cooled to ambient temperature and the volatiles were removed under reduced pressure. The residual oil was treated with 2N NaOH until basic and the aqueous extracted well with dichloromethane. The combined organic extracts were dried over sodium sulfate and concentrated under reduced pressure to give 32.15 gm (64.5%) of the title compound as a brown oil.

MS (m/e): 126(M+)

$^1$H-NMR (DMSO-$d_6$): δ7.45 (s, 1H); 7.25 (s, 1H); 4.65 (t, 1H); 3.75 (s,3H); 3.55 (m, 2H); 2.55 (t, 2H).

1-methyl-4-(2-methanesulfonyloxethyl)pyrazole

To a solution of 16.0 gm (127 mMol) 2-(1-methyl-3-pyrazolo)-1-ethanol and 27 mL (193 mMol) triethylamine in 550 mL tetrahydrofuran were added 10.8 mL (140 mMol) methanesulfonyl chloride with icebath cooling. Once the addition was complete, the reaction mixture was stirred at ambient for 4 hours. The volatiles were then removed under reduced pressure and the residue partitioned between water and dichloromethane. The organic phase was washed with water followed by saturated aqueous sodium chloride and the remaining organics dried over sodium sulfate. The solvent was removed under reduced pressure to give a crude yield of 28.4 gm of the title compound as a brown oil. The product was used without further purification.

5-fluoro-3-[1,2,3,6-tetrahydro-4-pyridyl]-1H-indole

To a solution of 74 gm potassium hydroxide in 673 mL methanol were added 10.0 gm (74 mMol) 5-fluoroindole and 23.3 gm (151 mMol) 4-piperidone.HCl.H$_2$O. The reaction mixture was stirred at reflux for 18 hours. The reaction mixture was diluted with 1.3 L of water and the resulting precipitate recovered by filtration and dried under reduced pressure to give 10.75 gm (67.2%) of 5-fluoro-3-[1,2,5,6-tetrahydro-4-pyridyl]-1H-indole as a yellow solid.

5-fluoro-3-(4-piperidinyl)-1H-indole

To a solution of 10.75 gm (50 mMol) 5-fluoro-3-[1,2,5,6-tetrahydro-4-pyridyl]-1H-indole in 500 mL ethanol were added 2.0 gm 5% palladium on carbon and the reaction mixture hydrogenated at ambient temperature for 18 hours at an initial hydrogen pressure of 60 p.s.i. The reaction mixture was then filtered through a pad of celite and the filtrate concentrated under reduced pressure to give an off-white solid. The solid was recrystallized from methanol to give 8.31 gm (76.2%) of the title compound as a colorless solid.

m.p.=229°–230° C.

MS (m/e): 218(M+)

Calculated for $C_{13}H_{15}N_2F$: Theory: C, 71.53; H, 6.93; N, 12.83. Found: C, 71.81; H, 7.02; N, 12.80.

Alkylation

To a solution of 2.0 gm (9.2 mMol) 5-fluoro-3-(4-piperidinyl)-1H-indole and 2.4 gm (23 mMol) sodium carbonate in 50 mL dimethylformamide were added 1.87 gm (9.2 mMol) 1-methyl-4-(2-methanesulfonyloxyethyl)pyrazole in 5 mL dimethylformamide. The reaction mixture was stirred at 100° C. for 18 hours. The reaction mixture was cooled to ambient and the solvent removed under reduced pressure. The residue was partitioned between dichloromethane and water and the phases separated. The organic phase was washed well with water followed by saturated aqueous sodium chloride. The remaining organic phase was dried over sodium sulfate and concentrated under reduced pressure. The residual oil was subjected to silica gel chromatography, eluting with 20:1 dichloromethane:methanol. Fractions shown to contain the desired compound were combined and concentrated under reduced pressure to give a yellow oil. The oil was converted to the hydrochloride salt and was crystallized from ethyl acetate/methanol. 1.61 gm (51.1%) of Compound II were recovered as colorless crystals.

m.p.=239° C.

MS (m/e): 326(M+)

Calculated for $C_{19}H_{23}N_4F.HCl$: Theory: C, 62.89; H, 6.67; N, 15.44. Found: C, 62.80; H, 6.85; N, 15.40.

Compound III 5-hydroxy-3-(4-piperidinyl)-1-H-indole oxalate

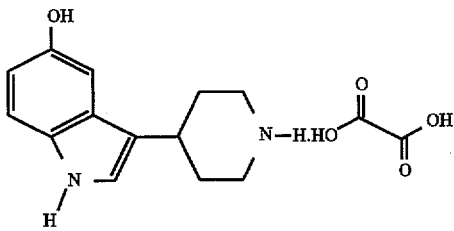

Compound III is available by the following procedure.

5-benzyloxy-3-[1,2,5,6-tetrahydro-4-pyridyl]-1-H-indole

Starting with 5.0 gm (22 mMol) 5-benzyloxyindole and 6.88 gm (45 mMol) 4-piperidone.HCl.H$_2$O, 6.53 gm (97.6%) of 5-benzyloxy-3-[1,2,5,6-tetrahydro-4-pyridyl]-1-H-indole were recovered as a light yellow solid by the procedure described for the synthesis of 5-fluoro-3-[1,2,5,6-tetrahydro-4-pyridyl]-1-H-indole supra. The material was used in the subsequent step without further purification.

Hydrogenation/Hydrogenolysis

To a solution of 1.23 gm (4 mMol) 5-benzyloxy-3-[1,2,5,6-tetrahydro-4-pyridyl]-1H-indole in 50 mL 1:1 tetrahydrofuran:ethanol were added 0.3 gm 5% palladium on carbon and the reaction mixture hydrogenated at ambient temperature for 18 hours with an initial hydrogen pressure of 60 p.s.i. The reaction mixture was then filtered through a celite pad and the filtrate concentrated under reduced pressure. The residue was converted to the oxalate salt and 0.98 gm (80.0%) of Compound III were recovered as a brown foam.

m.p.=67° C.

MS (m/e): 216(M$^+$)

Calculated for $C_{13}H_{16}N_2O.C_2H_2O_4$: Theory: C, 58.81; H, 5.92; N, 9.14. Found: C, 58.70; H, 5.95; N, 9.39.

Compound IV 8-chloro-2-diethylamino-1,2,3,4-tetrahydronaphthalene hydrochloride

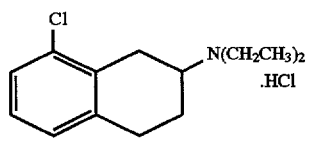

Compound IV is available by the following procedure.

8-chloro-2-tetralone

A mixture of 30.0 gm (0.176 mole) of o-chlorophenylacetic acid and 40.0 mL of thionyl chloride was stirred at ambient temperature for 18 hours. The volatiles were then removed in vacuo to give 32.76 gm (99.0 %) of o-chlorophenylacetyl chloride as a transparent, pale yellow, mobile liquid.

NMR (CDCl$_3$): 7.5–7.1 (m, 4H), 4.2 (s, 2H).

To a slurry of 46.5 gm (0.348 mole) AlCl$_3$ in 400 mL dichloromethane at −78° C. was added a solution of 32.76 gm (0.174 mole) of the previously prepared o-chlorophenylacetyl chloride in 100 mL dichloromethane dropwise over 1 hour. The dry ice/acetone bath then was replaced with an ice/water bath and ethylene was bubbled into the reaction mixture during which time the temperature rose to 15° C. The ethylene addition was discontinued at the end of the exotherm and the reaction mixture was stirred at about 5° C. for 4 hours. Ice was then added to the reaction mixture to destroy aluminum complexes. Upon termination of the exotherm, the reaction mixture was diluted with 500 mL of water and stirred vigorously until all solids had dissolved. The phases were separated and the organic phase was washed with 3×400 mL 1N hydrochloric acid and 2×400 mL saturated aqueous sodium bicarbonate. The remaining organic phase was then dried over sodium sulfate and concentrated in vacuo to give a pale orange residue. The residue was dissolved in 1:1 hexane:diethyl ether and was poured over a flash silica column which was then eluted with 1:1 hexane:diethyl ether to give a light yellow residue which was crystallized from 4:1 hexane:diethyl ether to give 10.55 gm of the title compound.

NMR (CDCl$_3$): 7.5–7.2 (m, 3H), 3.7 (s, 2H), 3.3–3.0 (t, J=7 Hz, 2H), 2.8–2.4 (t, J=7 Hz, 2H).

MS: 180(60), 165(9), 138(100), 117(52), 115(50), 103 (48), 89(20), 76(25), 74(18), 63(30), 57(9), 52(28), 51(20), 42(6), 39(32).

IR (nujol mull): 2950 cm$^{-1}$, 2927 cm$^{-1}$, 1708 cm$^{-1}$, 1464 cm$^{-1}$, 1450 cm$^{-1}$, 1169 cm$^{-1}$, 1141 cm$^{-1}$.

Reductive Amination

To a solution of 0.5 gm (2.78 mMol) 8-chloro-2-tetralone in 25 mL cyclohexane were added 1.4 mL (13.9 mMol) diethylamine followed by 0.1 gm p-toluenesulfonic acid monohydrate. The reaction mixture was then heated at reflux with constant water removal (Dean-Stark Trap) for 18 hours. The reaction mixture was then cooled to ambient and the volatiles removed under reduced pressure. The residue was then dissolved in 15 mL methanol to which were then added 1.5 mL acetic acid followed by the portionwise addition of 0.5 gm sodium borohydride. The reaction mixture was then stirred for 1 hour at ambient.

The reaction mixture was then diluted with 20 mL 10% HCl and stirred for an additional hour. The mixture was then extracted with diethyl ether and the remaining aqueous phase was poured over ice, made basic with ammonium hydroxide and extracted well with dichloromethane. These extracts were combined, dried over sodium sulfate and concentrated under reduced pressure. The residue was redissolved in dichloromethane and subjected to chromatography over basic alumina, eluting with dichloromethane. Fractions shown to contain product were combined and concentrated under reduced pressure. The residual oil was dissolved in diethyl ether and the solution saturated with hydrogen chloride. The viscous residue was crystallized from acetone/diethyl ether to give 0.20 gm (23.2 %) of Compound IV as colorless crystals.

m.p.=158°–159° C.

MS (m/e): 273

Calculated for $C_{14}H_{21}NCl.HCl$: Theory: C, 61.32; H, 7.72; N, 5.11. Found: C, 61.62; H, 7.94; N, 5.03.

Compound V

6-hydroxy-3-dimethylamino-1,2,3,4-tetrahydrocarbazole

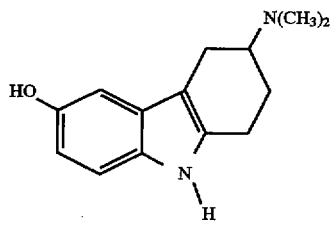

Compound V is available by the following procedure.

4-dimethylamino-1-cyclohexanone ethylene ketal

To a solution of 5.0 gm (32 mMol) 1,4-cyclohexanedione mono-ethylene ketal and 10.80 gm (240 mMol) dimethylamine were added 2.0 mL acetic acid and the mixture was stirred at 0° C. for 1.5 hours. To this solution were then added 3.62 gm (58 mMol) sodium cyanoborohydride and the reaction stirred for an additional hour at ambient. The pH of the reaction mixture was adjusted to ~7 with 16 mL acetic acid and stirred 18 hours at ambient. The volatiles were removed under reduced pressure and the residue dissolved in cold 5% tartaric acid solution and then the aqueous phase was made basic with 5N sodium hydroxide. This aqueous phase was extracted well with dichloromethane. These organic extracts were combined and concentrated under reduced pressure to give 5.04 gm (85%) of the title compound as an oil.

4-dimethylamino-1-cyclohexanone 4.96 gm (26.8 mMol) 4-dimethylamino-1-cyclohexanone ethylene ketal were dissolved in 50 mL formic acid and the solution stirred at reflux for 18 hours. The reaction mixture was then cooled to ambient and the volatiles removed under reduced pressure to give 3.78 gm (100%) of the title compound.

6-benzyloxy-3-dimethylamino-1,2,3,4-tetrahydrocarbazole

To a solution of 3.78 gm (26.8 mMol) 4-dimethylamino-1-cyclohexanone and 6.69 gm (26.8 mMol) 4-benzyloxyphenylhydrazine hydrochloride in 50 mL ethanol were added 2.17 mL (26.8 mMol) pyridine. To this solution were added 5×10 mL portions of water and the reaction mixture then stored at 0° C. for 18 hours. The reaction mixture was then diluted with an additional 50 mL of water and the mixture extracted well with dichloromethane. The combined organic extracts were dried over sodium sulfate and the volatiles removed under reduced pressure. The residual oil was subjected to flash silica gel chromatography, eluting with 9:1 chloroform:methanol. Fractions shown to contain the desired product were combined and concentrated under reduced pressure to give 2.14 gm (24.9%) of the title compound.

Hydrogenolysis

To a solution of 2.14 gm (6.7 mMol) 6-benzyloxy-3-dimethylamino-1,2,3,4-tetrahydrocarbazole in 50 mL ethanol were added 0.20 gm 10% palladium on carbon and the reaction mixture was hydrogenated at ambient temperature with an initial hydrogen pressure of 40 p.s.i. After 5 hours an additional charge of 0.20 gm 10% palladium on carbon were added and the reaction mixture repressurized with hydrogen to 40 p.s.i. for 4 hours. The reaction mixture was then filtered through a pad of celite and the filtrate concentrated under reduced pressure. The residue was subjected to Florisil chromatography, eluting with 9:1 chloroform:methanol. Fractions shown to contain the desired compound were combined and concentrated under reduced pressure. The residue was again subjected to Florisil chromatography, eluting with a gradient consisting of chloroform containing 2–10% methanol. Fractions shown to contain product were combined and concentrated under reduced pressure to give Compound V as a crystalline solid.
MS (m/e): 230(M$^+$)
Calculated for $C_{14}H_{18}N_2O$: Theory: C, 73.01; H, 7.88; N, 12.16. Found: C, 72.75; H, 7.83; N, 11.97.

To establish that the 5-HT$_{1F}$ receptor subtype is responsible for mediating neurogenic meningeal extravasation which leads to the pain of migraine, the binding affinity of the panel compounds to serotonin receptors was measured first using standard procedures. For example, the ability of a compound to bind to the 5-HT$_{1F}$ receptor subtype was performed essentially as described in N. Adham, et al., *Proceedings of the National Academy of Sciences (USA)*, 90, 408–412 (1993). For comparison purposes, the binding affinities of compounds to other serotonin receptors were determined essentially as described below except that different cloned receptors were employed in place of the 5-HT$_{1F}$ receptor clone employed therein.

Membrane Preparation

Membranes were prepared from transfected Ltk- cells which were grown to 100% confluency. The cells were washed twice with phosphate-buffered saline, scraped from the culture dishes into 5 mL of ice-cold phosphate-buffered saline, and centrifuged at 200×g for 5 minutes at 4° C. The pellet was resuspended in 2.5 mL of ice-cold Tris buffer (20 mM Tris HCl, pH=7.4 at 23° C., 5 mM EDTA) and homogenized with a Wheaton tissue grinder. The lysate was subsequently centrifuged at 200×g for 5 minutes at 4° C. to pellet large fragments which were discarded. The supernatant was collected and centrifuged at 40,000×g for 20 minutes at 4° C. The pellet resulting from this centrifugation was washed once in ice-cold Tris wash buffer and resuspended in a final buffer containing 50 mM Tris HCl and 0.5 mM EDTA, pH=7.4 at 23° C. Membrane preparations were kept on ice and utilized within two hours for the radioligand binding assays. Protein concentrations were determined by the method of Bradford (*Anal. Biochem.*, 72, 248–254 (1976)).

Radioligand Binding

[$^3$H 5-HT] binding was performed using slight modifications of the 5-HT$_{1D}$ assay conditions reported by Herrick-Davis and Titeler (*J. Neurochem.*, 50, 1624–1631 (1988)) with the omission of masking ligands. Radioligand binding studies were achieved at 37° C. in a total volume of 250 µL of buffer (50 mM Tris, 10 mM MgCl$_2$, 0.2 mM EDTA, 10Mµ pargyline, 0.1% ascorbate, pH=7.4 at 37° C.) in 96 well microtiter plates. Saturation studies were conducted using [$^3$H]5-HT at 12 different concentrations ranging from 0.5 nM to 100 nM. Displacement studies were performed using 4.5–5.5 nM [$^3$H]5-HT. The binding profile of drugs in competition experiments was accomplished using 10–12 concentrations of compound. Incubation times were 30 minutes for both saturation and displacement studies based upon initial investigations which determined equilibrium binding conditions. Nonspecific binding was defined in the presence of 10 µM 5-HT. Binding was initiated by the addition of 50 µL membrane homogenates (10–20 µg). The reaction was terminated by rapid filtration through presoaked (0.5% poylethyleneimine) filters using 48R Brandel Cell Harvester (Gaithersburg, Md.). Subsequently, filters were washed for 5 seconds with ice cold buffer (50 mM Tris HCl, pH=7.4 at 4° C.), dried and placed into vials containing 2.5 mL Readi-Safe (Beckman, Fullerton, Calif.) and radioactivity was measured using a Beckman LS 5000TA liquid scintillation counter. The efficiency of counting of [$^3$H]5-HT averaged between 45–50%. Binding data was analyzed by computer-assisted nonlinear regression analysis (Accufit and Accucomp, Lunden Software, Chagrin Falls, Ohio). $IC_{50}$ values were converted to $K_i$ values using the Cheng-Prusoff equation (*Biochem. Pharmacol.*, 22, 3099–3108 (1973). All experiments were performed in triplicate. The results of these binding experiments are summarized in Table I.

TABLE I

| BINDING TO SEROTONIN (5-HT$_1$) RECEPTOR SUBTYPES ($K_i$ nM) | | | | |
|---|---|---|---|---|
| Compound | 5-HT$_{1D\alpha}$ | 5-HT$_{1D\beta}$ | 5-HT$_{1B}$ | 5-HT$_{1F}$ |
| I | 4.8 | 9.6 | 2520.0 | 25.7 |
| II | 21.7 | 53.6 | 50.3 | 2.5 |
| III | 163.2 | 196.5 | 3.9 | 22.0 |
| IV | 13.5 | 145.3 | 813.0 | 129.2 |
| V | 791.0 | 1683.0 | 73.6 | 10.3 |

As was reported by R. L. Weinshank, et al., WO93/14201, the 5-HT$_{1F}$ receptor is functionally coupled to a G-protein as measured by the ability of serotonin and serotonergic drugs to inhibit forskolin stimulated cAMP production in NIH$_3$T3 cells transfected with the 5-HT$_{1F}$ receptor. Adenylate cyclase activity was determined using standard techniques. A maximal effect is achieved by serotonin. An $E_{max}$ is determined by dividing the inhibition of a test compound by the maximal effect and determining a percent inhibition. (N. Adham, et al., supra,; R. L. Weinshank, et al., *Proceedings of the National Academy of Sciences (USA)*, 89,3630–3634 (1992)), and the references cited therein.

Measurement of cAMP formation

Transfected NIH$_3$T3 cells (estimated Bmax from one point competition studies=488 fmol/mg of protein) were incubated in DMEM, 5 mM theophylline, 10 mM HEPES (4-[2-hydroxyethyl]-1-piperazineethanesulfonic acid) and 10 µM for pargyline 20 minutes at 37° C., 5% CO$_2$. Drug concentration-effect curves were then conducted by adding 6 different final concentrations of drug, followed immediately by the addition of forskolin (10 µM).Subsequently, the cells were incubated for an additional 10 minutes at 37° C., 5% CO$_2$. The medium was aspirated and the reaction was stopped by the addition of 100 mM HCl. To demonstrate competitive antagonism, a concentration-response curve for 5-HT was measured in parallel, using a fixed dose of methiothepin (0.32 µM. The plates were stored at 4° C. for 15 minutes and then centrifuged for 5 minutes at 500×g to pellet cellular debris, and the supernatant was aliquoted and stored at −20° C. before assessment of cAMP formation by radioimmunoassay (cAMP radioimmunoassay kit; Advanced Magnetics, Cambridge, Mass.). Radioactivity was quantified using a Packard COBRA Auto Gamma counter, equipped with data reduction software. All of the compounds tested were found to be agonists at the 5-HT$_{1F}$ receptor in the cAMP assay.

The following test was performed to determine the ability of the panel compounds to inhibit protein extravasation which is a functional assay for the neuronal mechanism of migraine. The results of this assay are summarized in Table II.

Protein extravasation assay

Harlan Sprague-Dawley rats (225–325 g) or guinea pigs from Charles River Laboratories (225–325 g) were anesthetized with sodium pentobarbital intraperitoneally (65 mg/kg or 45 mg/kg respectively) and placed in a stereotaxic frame (David Kopf Instruments) with the incisor bar set at −3.5 mm for rats or −4.0 mm for guinea pigs. Following a midline sagital scalp incision, two pairs of bilateral holes were drilled through the skull (6 mm posterially, 2.0 and 4.0 mm laterally in rats; 4 mm posteriorly and 3.2 and 5.2 mm laterally in guinea pigs, all coordinates referenced to bregma). Pairs of stainless steel stimulating electrodes, insulated except at the ends (Rhodes Medical Systems, Inc.), were lowered through the holes in both hemispheres to a depth of 9 mm (rats) or 10.5 mm (guinea pigs) from dura.

The femoral vein was exposed and a dose of the test compound was injected intravenously (1 mL/kg). Approximately 7 minutes later, a 50 mg/kg dose of Evans Blue, a fluorescent dye, was also injected intravenously. The Evans Blue complexed with proteins in the blood and functioned as a marker for protein extravasation. Exactly 10 minutes post-injection of the test compound, the left trigeminal ganglion was stimulated for 3 minutes at a current intensity of 1.0 mA (5 Hz, 4 msec duration) with a Model 273 potentiostat/galvanostat (EG&G Princeton Applied Research).

Fifteen minutes following stimulation, the animals were killed and exsanguinated with 20 mL of saline. The top of the skull was removed to facilitate the collection of the dural membranes. The membrane samples were removed from both hemispheres, rinsed with water, and spread flat on microscopic slides. Once dried, the tissues were coverslipped with a 70% glycerol/water solution.

A fluorescence microscope (Zeiss) equipped with a grating monchromator and a spectrophotometer was used to quantify the amount of Evans Blue dye in each sample. An excitation wavelength of approximately 535 nm was utilized and the emission intensity at 600 nm was determined. The microscope was equipped with a motorized stage and also interfaced with a personal computer. This facilitated the computer-controlled movement of the stage with fluorescence measurements at 25 points (500µm steps) on each dural sample. The mean and standard deviation of the measurements were determined by the computer.

The extravasation induced by the electrical stimulation of the trigeminal ganglion was an ipsilateral effect (i.e. occurs only on the side of the dura in which the trigeminal ganglion was stimulated). This allows the other (unstimulated) half of the dura to be used as a control. The ratio of the amount of extravasation in the dura from the stimulated side compared to the unstimulated side was calculated. Saline controls yielded a ratio of approximately 2.0 in rats and 1.8 in guinea pigs. In contrast, a compound which effectively prevented the extravasation in the dura from the stimulated side would have a ratio of approximately 1.0. A dose-response curve was generated and the dose that inhibited the extravasation by 50% ($ID_{50}$) was approximated.

TABLE II

| Inhibition of Protein Extravasation ($ID_{50}$ mMol/kg) | |
|---|---|
| Compound | i.v. $ID_{50}$ (mMol/kg) |
| I | $2.6 \times 10^{-8}$ |
| II | $8.0 \times 10^{-10}$ |
| III | $8.9 \times 10^{-9}$ |

TABLE II-continued

| Inhibition of Protein Extravasation ($ID_{50}$ mMol/kg) | |
|---|---|
| Compound | i.v. $ID_{50}$ (mMol/kg) |
| IV | $1.2 \times 10^{-7}$ |
| V | $8.7 \times 10^{-9}$ |

To determine if a relationship existed between the binding affinity to each of the $5\text{-HT}_{1D\alpha}$, $5\text{-HT}_{1D\beta}$, $5\text{-HT}_{1E}$ and $5\text{-HT}_{1F}$ receptors and neuronal protein extravasation, binding affinity for each receptor subtype was plotted against their $ID_{50}$ in the protein extravasation model. A linear regression analysis was performed on each set of data and a correlation factor, $R^2$, was then calculated. The results of this analysis are summarized in Table III.

TABLE III

Correlation Factor ($R^2$) for Specific $5\text{-HT}_1$ Subtype Binding Affinity vs Inhibition of Protein Extravasation

| $5\text{-HT}_1$ Subtype | Correlation Factor ($R^2$) |
|---|---|
| $5\text{-HT}_{1D\alpha}$ | 0.07 |
| $5\text{-HT}_{1D\beta}$ | 0.001 |
| $5\text{-HT}_{1E}$ | 0.31 |
| $5\text{-HT}_{1F}$ | 0.94 |

An ideally linear relationship would generate a correlation factor of 1.0, indicating a cause and effect relationship between the two variables. The experimentally determined correlation factor between inhibition of neuronal protein extravasation and $5\text{-HT}_{1F}$ binding affinity is 0.94. This nearly ideal dependence of the $ID_{50}$ in the protein extravasation model on binding affinity to the $5\text{-HT}_{1F}$ receptor clearly demonstrates that the $5\text{-HT}_{1F}$ receptor mediates the inhibition of neuronal protein extravasation resulting from stimulation of the trigeminal ganglia.

As defined supra, partial agonists of the $5\text{-HT}_{1F}$ receptor may also be useful for the method of this invention. Dihydroergotamine, for example, is a commercially available treatment for migraine of the following structure:

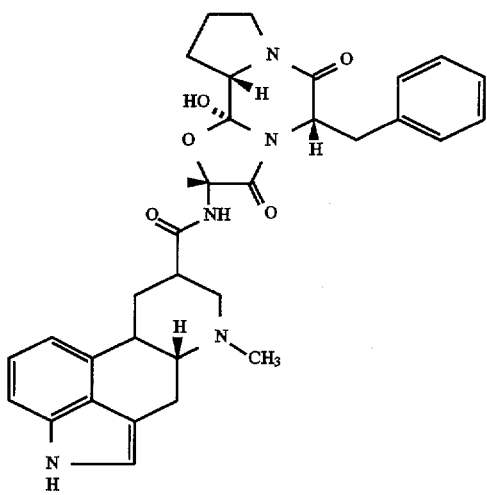

Dihydroergotamine, when tested in the above assays, has been shown to bind at the $5\text{-HT}_{1F}$ receptor ($K_i$=276 nM) and yet was shown in the cAMP assay to be a partial agonist at the $5\text{-HT}_{1F}$ receptor ($E_{max}$=49.5%). When tested in the neuronal protein extravasation assay, dihydroergotamine was shown to be a fully effective inhibitor of neuronal protein extravasation ($ID_{50}$=2.43×10$^{-8}$ mMol/kg), reaching a ratio 1.0 when sides of the dura were compared. Dihydroergotamine is known to be a potent vasoconstrictor (Goodman and Gilman, The *Pharmacological Basis of Therapeutics*, 8th Edition, 943–947, Pergamon Press, New York, (1990)), and as such would not be a compound useful for the present invention.

While a compound must have agonist activity at the $5\text{-HT}_{1F}$ receptor to be useful for the method of this invention, it is imperative that it not demonstrate appreciable vasoconstrictive effects. Panel compounds I, II, IV and V were subsequently tested in the following assay to measure their ability to mediate vasoconstriction in the rabbit saphenous vein. The data from this assay are summarized in Table IV.

Rabbit Saphenous Vein Contraction

Male New Zealand White rabbits (3–6 lbs) (Hazleton, Kalamazoo, Mich.) were sacrificed by a lethal dose of sodium pentobarbital (325 mg) injected into the ear vein. Tissues were dissected free of connective tissue, cannulated in situ with polyethylene tubing (PE50, outside diameter= 0.97 mm) and placed in petri dishes containing Kreb's bicarbonate buffer (described infra). The tips of two 30-gauge stainless steel hypodermic needles bent into an L-shape were slipped into the polyetylene tubing. Vessels were gently pushed from the cannula onto the needles. The needles were then separated so that the lower one was attached with thread to a stationary glass rod and the upper one was tied with thread to the transducer.

Tissues were mounted in organ baths containing 10 mL of modified Krebs' solution of the following composition: 118.2 mMol NaCl, 4.6 mMol KCl, 1.6 mMol CaCl$_2$.H$_2$O, 1.2 mMol KH$_2$PO$_4$, 1.2 mMol MgSO$_4$, 10.0 mMol dextrose and 24.8 mMol NaHCO$_3$. Tissue bath solutions were maintained at 37° C. and aerated with 95% O$_2$ and 5% CO$_2$. An initial optimum resting force of 1 gm was applied to the saphenous vein. Isometric contractions were recorded as changes in grams of force on a Beckman Dynograph with Statham UC-3 transducers and microscale accessory attachments. Tissues were allowed to equilibrate 1 to 2 hours before exposure to drugs. Cumulative agonist concentration-response curves were generated in tissues and no tissue was used to generate more than two agonist concentration-response curves. All results were expressed as a mean EC$_{50}$ and the maximal response was expressed as a percentage of the response to 67 mM KCl administered initially in each tissue.

TABLE IV

| Rabbit Saphenous Vein Contraction | | |
|---|---|---|
| Compound | Rabbit Saphenous Vein Contraction EC$_{50}$ (M) | Rabbit Saphenous Vein Contraction (% Max. KCl)* |
| I | $6.6 \times 10^{-7}$ | 64.20 |
| II | $1.0 \times 10^{-6}$ | 13.72 |
| IV | $1.0 \times 10^{-6}$ | 67.16 |
| V | $>1.0 \times 10^{-4}$ | 12.44 |

*Either maximal response determined or response at $10^{-4}$ M, if maximal contraction not achieved.

This vasoconstriction assay measures two important parameters, saphenous vein contraction (EC$_{50}$) and maximal contraction as a % maximal KCl response. The saphenous vein contraction (EC$_{50}$) is a measure of the dose required to contract tissue to 50% of the maximal response that the specific compound is capable of mediating. The maximal response that the saphenous vein is capable of exhibiting is measured after administration of a high concentration (67 mM) of KCl. The % maximal KCl contraction is the ratio of the maximal response that the specific compound is capable of mediating divided by the maximal response that the tissue can produce.

The data presented in Tables II and IV clearly demonstrate that the panel compounds differ substantially in their ability to inhibit neuronal protein extravasation and to mediate vasoconstriction. The specificity required for the method of this invention is defined as a separation of the ability to mediate vasoconstriction relative to the 5-HT$_{1F}$ mediated inhibition of neuronal protein extravasation. A measure of this specificity is the ratio of vasoconstriction to efficacy in inhibition of neuronal protein extravasation. This ratio, defined as the Specificity Index, is presented in Table V for the panel compounds where:

$$\text{Specificity Index} = \frac{\text{Corrected Vasoconstriction } EC_{50} \, (M)}{\text{Extravasation } ID_{50} \, (\text{mMol/kg})}$$

TABLE V

Specificity Index
Vasoconstriction relative to 5-HT$_{1F}$ mediated inhibition of neuronal protein extravasation

| Compound | A<br>Extravasation<br>ID$_{50}$<br>(mMol/kg) | B<br>Corrected<br>Vasoconstriction<br>EC$_{50}$ (M)* | SPECIFICITY<br>INDEX<br>(RATIO B/A) |
|---|---|---|---|
| I | 2.6 × 10$^{-8}$ | 1.03 × 10$^{-8}$ | 0.40 |
| II | 8.0 × 10$^{-10}$ | 7.29 × 10$^{-8}$ | 91.12 |
| IV | 1.2 × 10$^{-7}$ | 1.49 × 10$^{-9}$ | 0.01 |
| V | 8.7 × 10$^{-9}$ | >8.03 × 10$^{-6}$ | >923.00 |

*To correct the EC$_{50}$ values for saphenous vein contraction so that the maximal contraction relative to KCl for each individual compound can be taken into consideration, the vasoconstriction ID$_{50}$ value is divided by the % maximum KCl contraction to give the "corrected vasoconstriction EC$_{50}$ (M)".

Compounds II and V exemplify the specificity typical for compounds useful for the method of this invention, with Specificity Indices of 91.12 and >923 respectively. Compounds I and IV, in comparison, while exhibiting a significant component of 5-HT$_{1F}$ activity, exhibit none of the desired specificity. Sumatriptan (Compound I), a commercial treatment for migraine, barely distinguishes between the two activities, demonstrating greater efficacy for vasoconstriction. Compound IV has a much greater ability to mediate vasoconstriction than to inhibit neuronal protein extravasation.

The suitability of a compound or composition for use in the method of the present invention, therefore, is determined as follows:

1. Demonstration of affinity for the 5-HT$_{1F}$ receptor using the radioligand binding method described above;

2. Once affinity for the 5-HT$_{1F}$ receptor is established, determination of agonist, partial agonist or antagonist character is determined by measurement in the previously described cAMP assay;

3. If the compound or composition is shown to be an agonist or partial agonist with an E$_{max}$ of at least about 50%, it is tested to measure efficacy in inhibition of protein extravasation and saphenous vein contraction using the assays previously described; and 4. Calculate the Specificity Index as shown above.

While a compound or composition with a Specificity Index greater than 1 is useful for the method of this invention, larger values for the Specificity Index are preferred. A larger Specificity Index indicates greater specificity for efficacy in inhibition of neuronal protein extravasation over vasoconstriction. The following ranges for the Specificity Index are representative of the specificity of compounds or compositions useful for the invention and are not meant to limit the invention in any way.

A Specificity Index greater than 1.
A Specificity Index of at least 5.
A Specificity Index in the range of 5–10,000.
A Specificity Index in the range of 5–1,000.
A Specificity Index in the range of 5–100.
A Specificity Index in the range of 5–10.
A Specificity Index of St least 10.
A Specificity Index in the range of 10–10,000.
A Specificity Index in the range of 10–1,000.
A Specificity Index in the range of 10–100.
A Specificity Index of at least 100.
A Specificity Index in the range of 100–10,000.
A Specificity Index in the range of 100–1,000.
A Specificity Index of at least 1,000.
A Specificity Index in the range of 1,000–10,000.
A Specificity Index of at least 10,000.
A Specificity Index in the range of 2,000–10,000.
A Specificity Index in the range of 2,000–5,000.
A Specificity Index in the range of 4,000–10,000.
A Specificity Index in the range of 6,000–10,000.
A Specificity Index in the range of 8,000–10,000.

In summary, the usefulness of a compound or a composition in a method for the treatment of the pain of migraine and associated disorders without substantial side effects caused by vasoconstriction is determined by its Specificity Index. The Specificity Index is the ratio of vasoconstriction to efficacy in inhibition of neuronal protein extravasation. Measurement of the ability of a compound or composition to inhibit neuronal protein extravasation is a functional assay for the physiological events leading to migraine pain. Neuronal protein extravasation has been shown to be inhibited by agonists of the 5-HT$_{1F}$ receptor.

While it is possible to administer a compound employed in the methods of this invention directly without any formulation, the compounds are usually administered in the form of pharmaceutical compositions comprising a pharmaceutically acceptable excipient and at least one active ingredient. These compositions can be administered by a variety of routes including oral, buccal, rectal, transdermal, subcutaneous, intravenous, intramuscular, and intranasal. Many of the compounds employed in the methods of this invention are effective as both injectable and oral compositions. Such compositions are prepared in a manner well known in the pharmaceutical art and comprise at least one active compound. See, e.g., REMINGTON'S PHARMACEUTICAL SCIENCES, (16th ed. 1980).

In making the compositions employed in the present invention the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient. The active compounds are generally effective over a wide dosage range. However, it will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms.

The following dosages are for purposes of example only and are not intended to limit the scope of the invention in any way. In some instances dosage levels below the amount of the example may be more than adequate, while in other cases still larger doses may be employed without causing any harmful side effect, provided that such larger doses are first divided into several smaller doses for administration throughout the day.

FORMULATION EXAMPLE 1

Hard gelatin capsules containing the following ingredients are prepared:

| Ingredient | Quantity (mg/capsule) |
| --- | --- |
| Compound II | 30.0 |
| Starch | 305.0 |
| Magnesium stearate | 5.0 |

The above ingredients are mixed and filled into hard gelatin capsules in 340 mg quantities.

FORMULATION EXAMPLE 2

A tablet formula is prepared using the ingredients below:

| Ingredient | Quantity (mg/tablet) |
| --- | --- |
| Compound V | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

FORMULATION EXAMPLE 3 a dry powder inhaler formulation is prepared containing the following components:

| Ingredient | Weight % |
| --- | --- |
| Compound II | 5 |
| Lactose | 95 |

The active mixture is mixed with the lactose and the mixture is added to a dry powder inhaling appliance.

FORMULATION EXAMPLE 4

Tablets, each containing 30 mg of active ingredient, are prepared as follows:

| Ingredient | Quantity (mg/tablet) |
| --- | --- |
| Compound V | 30.0 mg |
| Starch | 45.0 mg |
| Microcrystalline cellulose | 35.0 mg |
| Polyvinylpyrrolidone (as 10% solution in water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50°–60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

FORMULATION EXAMPLE 5

Capsules, each containing 40 mg of medicament are made as follows:

| Ingredient | Quantity (mg/capsule) |
| --- | --- |
| Compound II | 40.0 mg |
| Starch | 109.0 mg |

-continued

| Ingredient | Quantity (mg/capsule) |
|---|---|
| Magnesium stearate | 1.0 mg |
| Total | 150.0 mg |

The active ingredient, cellulose, starch, and magnesium stearate are blended, passed through a No. 20 mesh U.S. sieve, and filled into hard gelatin capsules in 150 mg quantities.

FORMULATION EXAMPLE 6

Suppositories, each containing 25 mg of active ingredient are made as follows:

| Ingredient | Amount |
|---|---|
| Compound V | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

FORMULATION EXAMPLE 7

Suspensions, each containing 50 mg of medicament per 5.0 ml dose are made as follows:

| Ingredient | Amount |
|---|---|
| Compound II | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 ml |

The medicament, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

FORMULATION EXAMPLE 8

Capsules, each containing 15 mg of medicament, are made as follows:

| Ingredient | Quantity (mg/capsule) |
|---|---|
| Compound V | 15.0 mg |
| Starch | 407.0 mg |
| Magnesium stearate | 3.0 mg |
| Total | 425.0 mg |

The active ingredient, cellulose, starch, and magnesium stearate are blended, passed through a No. 20 mesh U.S. sieve, and filled into hard gelatin capsules in 425 mg quantities.

FORMULATION EXAMPLE 9

An intravenous formulation may be prepared as follows:

| Ingredient | Quantity |
|---|---|
| Compound II | 250.0 mg |
| Isotonic saline | 1000 ml |

FORMULATION EXAMPLE 10

A topical formulation may be prepared as follows:

| Ingredient | Quantity |
|---|---|
| Compound V | 1–10 g |
| Emulsifying Wax | 30 g |
| Liquid Paraffin | 20 g |
| White Soft Paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solid.

FORMULATION EXAMPLE 11

Sublingual or buccal tablets, each containing 10 mg of active ingredient, may be prepared as follows:

| Ingredient | Quantity Per Tablet |
|---|---|
| Compound II | 10.0 mg |
| Glycerol | 210.5 mg |
| Water | 143.0 mg |
| Sodium Citrate | 4.5 mg |
| Polyvinyl Alcohol | 26.5 mg |
| Polyvinylpyrrolidone | 15.5 mg |
| Total | 410.0 mg |

The glycerol, water, sodium citrate, polyvinyl alcohol, and polyvinylpyrrolidone are admixed together by continuous stirring and maintaining the temperature at about 90° C. When the polymers have gone into solution, the solution is cooled to about 50°–55° C. and the medicament is slowly admixed. The homogenous mixture is poured into forms made of an inert material to produce a drug-containing diffusion matrix having a thickness of about 2–4 mm. This diffusion matrix is then cut to form individual tablets having the appropriate size.

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252, issued Jun. 11, 1991, herein incorporated by reference. Such patches may be constructed for continuous, pulsatile, or on demand delivery of pharmaceutical agents.

Frequently, it will be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system, used for the transport of biological factors to specific anatomical regions of the body, is described in U.S. Pat. No. 5,011,472, issued Apr. 30, 1991, which is herein incorporated by reference.

Indirect techniques, which are generally preferred, usually involve formulating the compositions to provide for drug latentiation by the conversion of hydrophilic drugs into lipid-soluble drugs or prodrugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions which can transiently open the blood-brain barrier.

The type of formulation employed for the administration of the compounds employed in the methods of the present invention may be dictated by the particular compounds employed, the type of pharmacokinetic profile desired from the route of administration and the compound(s), and the state of the patient.

We claim:

1. A method for the treatment or prevention of migraine in a mammal comprising administering to a mammal in need thereof an effective amount of a $5\text{-}HT_{1F}$ agonist which exhibits minimal vasoconstrictive properties.

2. A method as claimed in claim 1 in which the $5\text{-}HT_{1F}$ agonist possesses a Specificity Index in the range of 5–10,000.

3. A method as claimed in claim 1 in which the $5\text{-}HT_{1F}$ agonist possesses a Specificity Index in the range of 5–1,000.

4. A method as claimed in claim 1 in which the $5\text{-}HT_{1F}$ agonist possesses a Specificity Index in the range of 5–100.

5. A method as claimed in claim 1 in which the $5\text{-}HT_{1F}$ agonist possesses a Specificity Index in the range of 5–10.

6. A method as claimed in claim 1 in which the $5\text{-}HT_{1F}$ agonist possesses a Specificity Index of at least 10.

7. A method as claimed in claim 1 in which the $5\text{-}HT_{1F}$ agonist possesses a Specificity Index in the range of 10–10,000.

8. A method as claimed in claim 1 in which the $5\text{-}HT_{1F}$ agonist possesses a Specificity Index in the range of 10–1,000.

9. A method as claimed in claim 1 in which the $5\text{-}HT_{1F}$ agonist possesses a Specificity Index in the range of 10–100.

10. A method as claimed in claim 1 in which the $5\text{-}HT_{1F}$ agonist possesses a Specificity Index of at least 100.

11. A method as claimed in claim 1 in which the $5\text{-}HT_{1F}$ agonist possesses a Specificity Index in the range of 100–10,000.

12. A method as claimed in claim 1 in which the $5\text{-}HT_{1F}$ agonist possesses a Specificity Index in the range of 100–1,000.

13. A method as claimed in claim 1 in which the $5\text{-}HT_{1F}$ agonist possesses a Specificity Index of at least 1,000.

14. A method as claimed in claim 1 in which the $5\text{-}HT_{1F}$ agonist possesses a Specificity Index in the range of 1,000–10,000.

15. A method as claimed in claim 1 in which the $5\text{-}HT_{1F}$ agonist possesses a Specificity Index in the range of 2,000–10,000.

16. A method as claimed in claim 1 in which the $5\text{-}HT_{1F}$ agonist possesses a Specificity Index in the range of 2,000–5,000.

17. A method as claimed in claim 1 in which the $5\text{-}HT_{1F}$ agonist possesses a Specificity Index in the range of 4,000–10,000.

18. A method as claimed in claim 1 in which the $5\text{-}HT_{1F}$ agonist possesses a Specificity Index in the range of 6,000–10,000.

19. A method as claimed in claim 1 in which the $5\text{-}HT_{1F}$ agonist possesses a Specificity Index in the range of 8,000–10,000.

20. A method as claimed in claim 1 in which the $5\text{-}HT_{1F}$ agonist possesses a Specificity Index of at least 10,000.

* * * * *